(12) United States Patent
Hsieh (10) Patent No.: US 7,050,527 B2
(45) Date of Patent: May 23, 2006

(54) METHODS AND APPARATUS FOR ARTIFACT REDUCTION IN CONE BEAM CT IMAGE RECONSTRUCTION

(75) Inventor: Jiang Hsieh, Brookfield, WI (US)

(73) Assignee: G.E. Medical Systems Global Technology Company, LLC, Waukesha, WI (US)

(*) Notice: Subject to any disclaimer, the term of this patent is extended or adjusted under 35 U.S.C. 154(b) by 83 days.

(21) Appl. No.: 10/774,796

(22) Filed: Feb. 9, 2004

(65) Prior Publication Data

US 2005/0175144 A1 Aug. 11, 2005

(51) Int. Cl.
*A61B 6/03* (2006.01)

(52) U.S. Cl. .......................................... 378/4; 378/901

(58) Field of Classification Search ................ 378/4, 378/8, 15, 901; 382/131
See application file for complete search history.

(56) References Cited

U.S. PATENT DOCUMENTS

| | | | | |
|---|---|---|---|---|
| 5,128,864 A | * | 7/1992 | Waggener et al. | 378/14 |
| 5,293,312 A | * | 3/1994 | Waggener | 378/14 |
| 5,307,264 A | * | 4/1994 | Waggener et al. | 378/14 |
| 5,406,479 A | * | 4/1995 | Harman | 378/7 |
| 5,889,833 A | * | 3/1999 | Silver | 378/15 |
| 6,266,388 B1 | | 7/2001 | Hsieh | |
| 6,269,139 B1 | | 7/2001 | Hsieh | |
| 6,373,920 B1 | | 4/2002 | Hsieh | |
| 6,408,042 B1 | | 6/2002 | Hsieh | |
| 6,421,411 B1 | | 7/2002 | Hsieh | |
| 6,452,996 B1 | | 9/2002 | Hsieh | |
| 6,490,333 B1 | | 12/2002 | Hsieh | |
| 6,507,632 B1 | | 1/2003 | Hsieh | |
| 6,600,802 B1 | | 7/2003 | Hsieh | |
| 6,647,095 B1 | | 11/2003 | Hsieh | |
| 6,654,440 B1 | | 11/2003 | Hsieh | |
| 6,654,442 B1 | | 11/2003 | Hsieh | |
| 6,678,346 B1 | | 1/2004 | Hsieh | |
| 2003/0073893 A1 | | 4/2003 | Hsieh | |
| 2003/0185337 A1 | | 10/2003 | Hsieh | |
| 2003/0185345 A1 | | 10/2003 | Hsieh | |
| 2003/0223533 A1 | | 12/2003 | Hsieh et al. | |
| 2004/0252806 A1 | * | 12/2004 | Taguchi et al. | 378/4 |

* cited by examiner

*Primary Examiner*—David V Bruce
(74) *Attorney, Agent, or Firm*—Carl B. Horton, Esq.; Armstrong Teasdale LLP (57) ABSTRACT

In one aspect, a method for producing an image of an object utilizing a computed tomography (CT) imaging system includes axially scanning an object utilizing the CT imaging system to obtain more than 180° of projection data of the object. The method also includes weighting the projection data according to projection location and pixel location of an image to be reconstructed and reconstructing the image of the object utilizing the weighted projection data.

22 Claims, 7 Drawing Sheets

METHODS AND APPARATUS FOR ARTIFACT REDUCTION IN CONE BEAM CT IMAGE RECONSTRUCTION

BACKGROUND OF THE INVENTION

This invention relates generally to computed tomography (CT) imaging, and more particularly, to methods and apparatus for artifact reduction in a CT systems that are particularly useful for such systems having a wide bore geometry.

Although the Feldkamp algorithm has been shown to be effective in combating cone beam artifacts for moderate cone angles, it has a disadvantage of reduced z-axis coverage relative to some other image reconstruction methods. For example to ensure artifact-free reconstruction, every voxel in an image must be sampled by all projections. In practice, to obtain a continuous reconstruction volume with multiple axial scans, the reconstructed volume for each scan is limited, as is the distance between adjacent axial scans. For example, in at least one known CT system, the cylindrical volume that can be covered by each axial scan is limited to 10.8 mm. To obtain a continuous coverage of an organ, the distance between adjacent scans is limited to 10.8 mm, which is half the detector z-coverage at the isocenter. To reconstruct a volume of 20 mm, extrapolation has to be performed to utilize the FDK (Feldkamp) reconstruction algorithm. However, this extrapolation introduces artifacts into the reconstructed image.

BRIEF DESCRIPTION OF THE INVENTION

Some configurations of the present invention therefore provide a method for producing an image of an object utilizing a computed tomography (CT) imaging system. The method includes axially scanning an object utilizing the CT imaging system to obtain more than 180° of projection data of the object, weighting the projection data according to projection location and pixel location of an image to be reconstructed, and reconstructing the image of the object utilizing the weighted projection data.

In some configurations, the present invention provides a method for producing an image of an object utilizing a computed tomography (CT) imaging system, wherein the method includes axially scanning an object utilizing the CT imaging system to obtain more than 180° of projection data of the object. The method further includes weighting the projection data according to projection location, and reconstructing an image of the object utilizing the weighted projected data in a Cartesian coordinate system.

Still other configurations of the present invention provide a method for producing an image of an object utilizing a computed tomography (CT) imaging system. These configurations include axially scanning an object utilizing the CT imaging system to obtain more than 180° of projection data of the object, selecting a range of projections in accordance with locations of pixels of an image of the object to be reconstructed, and reconstructing the image of the object utilizing the selected range of projections.

Some configurations of the present invention provide a computed tomography imaging system having a detector array and a radiation source. To produce an image of an object, the system is configured to axially scan an object to obtain more than 180° of projection data of the object. The imaging system is also configured to weight the projection data according to projection location and pixel location in an image to be reconstructed, and to reconstruct an image of the object utilizing the weighted projection data.

Moreover, some configurations of the present invention provide a computed tomography imaging system having a detector array and a radiation source, wherein the imaging system is configured to axially scan an object to obtain more than 180° of projection data of the object. The imaging system is further configured to weight the projection data according to projection location, and to reconstruct an image of the object utilizing the weighted projection data in a Cartesian coordinate system.

Yet other configurations of the present invention provide a computed tomography imaging system having a detector array and a radiation source. To produce an image of an object, the imaging system in these configurations is configured to axially scan an object to obtain more than 180° of projection data of the object. The imaging system is further configured to select a range of projections in accordance with locations of pixels of an image of the object to be reconstructed, and to reconstruct the image of the object utilizing the selected range of projections.

Various configurations of the present invention significantly reduce or eliminate objectionable cone beam artifacts in images produced from data obtained in axial CT scans. Thus, continuous coverage can be obtained with increased distance between adjacent axial scans relative to known methods and apparatus that attempt to reduce cone beam artifacts for moderate cone angles.

DETAILED DESCRIPTION OF THE INVENTION

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube or other type of display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
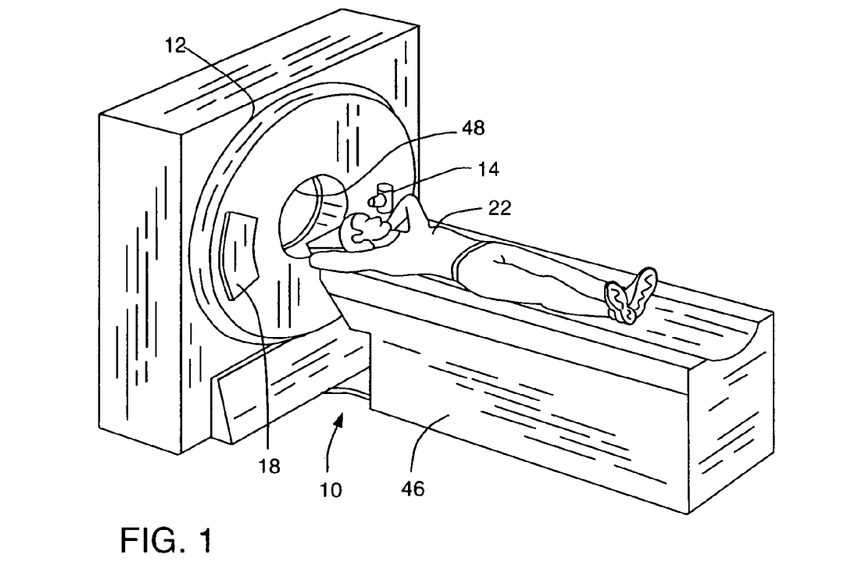
FIG. 1 is a pictorial view of a configuration of a CT imaging system.
Figure 2:
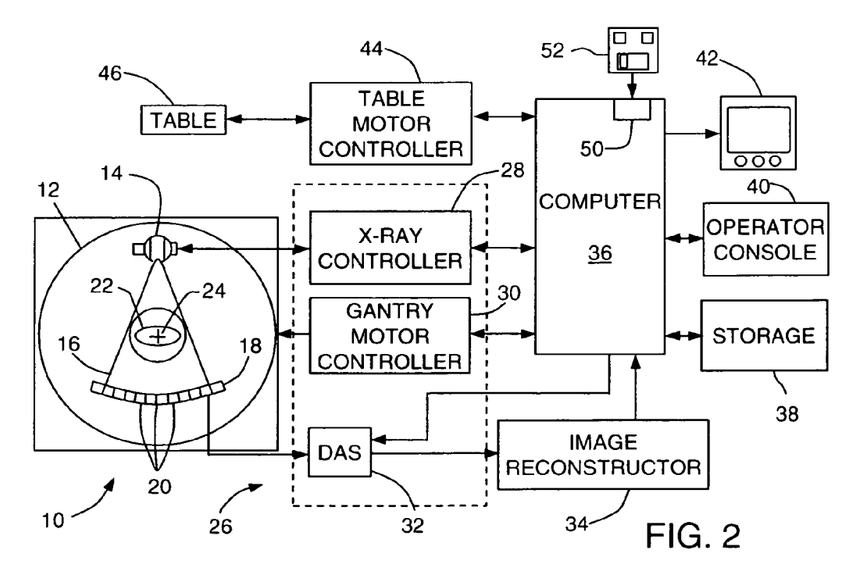
FIG. 2 is a block schematic diagram of the system illustrated in FIG. 1.

Referring to FIG. 1 and FIG. 2, a multi-slice scanning imaging system, for example, a Computed Tomography (CT) imaging system 10, is shown as including a gantry 12 representative of a "third generation" CT imaging system. Gantry 12 has a radiation source 14 which may be an x-ray tube 14 (also called x-ray source 14 herein) that projects a beam of radiation 16 toward a detector array 18 on the opposite side of gantry 12. (Configurations of the present invention are not limited to x-ray sources or x-ray radiation, although the configuration of CT imaging system 10 shown in FIG. 1 and FIG. 2 utilizes an x-ray source and x-ray radiation.) Detector array 18 is formed by a plurality of detector rows (not shown) including a plurality of detector elements 20 which together sense the radiation (i.e., in the configuration described herein, projected x-rays) that passes through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube or other type of display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a memory storage device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

A technical effect of the present invention is the production of an image or images of a patient or object 22 in which artifacts in the image or images are reduced. The technical effect is achieved by a user scanning an object or patient 22 utilizing a CT imaging system 10 and operating CT imaging system 10 to reconstruct images of the scanned object.

Figure 3:
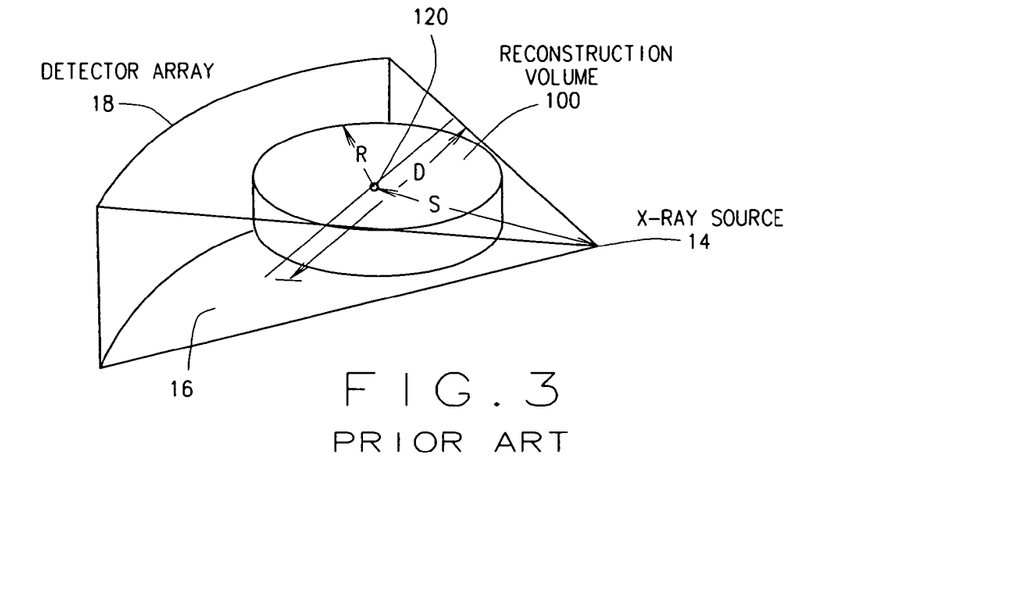
FIG. 3 is an illustration of the geometry of reduced volume coverage in prior art configurations of step-and-shoot multi-slice CT imaging systems.
Figure 4:
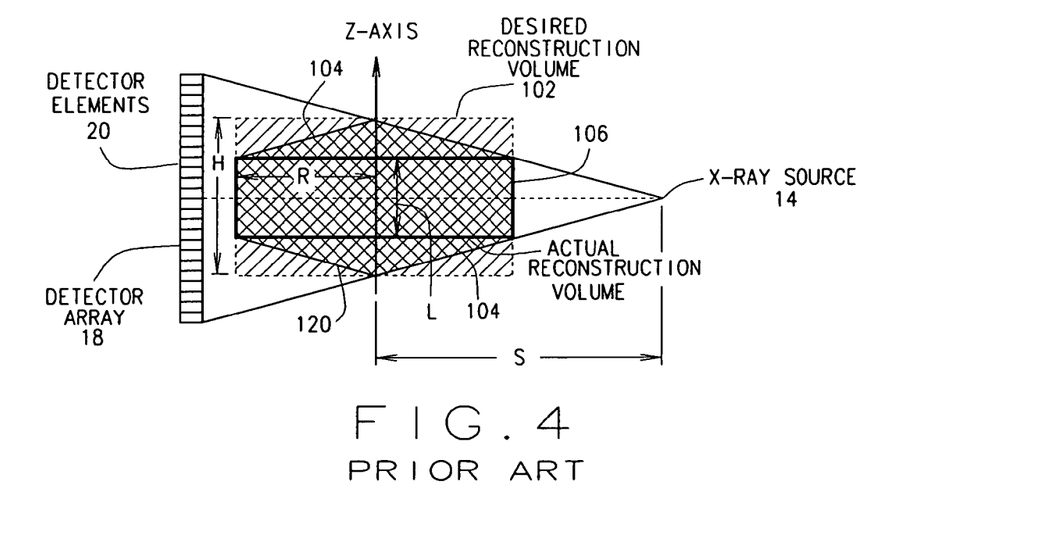
FIG. 4 is an illustration of desired and actual reconstruction volumes in prior art configurations of step-and-shoot multi-slice CT imaging systems.

Although the Feldkamp algorithm has been shown to be effective in combating cone beam artifacts for moderate cone angles, it has a disadvantage of reduced z-axis coverage relative to some other image reconstruction methods. For example, and referring to FIG. 3, a cylindrical region 100 representing a reconstructed volume for an axial scan of a multi-slice CT scanning apparatus 10 is shown. Referring to FIG. 4, a rectangle representing a desired reconstruction area 102 is shown. Height H of rectangle 102 is identical to the projected height of detector 18 at isocenter 120. For an FDK-type reconstruction algorithm in which $2\pi$ projection is used, every voxel in an image must be sampled by all projections. A volume satisfying this condition is represented by trapezoid 104. In practice, to obtain a continuous reconstruction volume with multiple axial scans, the reconstructed volume for each scan is limited to a rectangle 106 shown in heavy outline enclosed within trapezoid 104. As a result, the distance between adjacent axial scans cannot be larger than the length L of rectangle 106.

Denoting the projected detector width at the isocenter by D, the source to isocenter distance by S, and the radius of the reconstruction field of view (FOV) (x-y) by R, the distance t between adjacent axial scans for continuous coverage must satisfy the condition:

$$t \leq \left(\frac{S-R}{S}\right)D \quad (1)$$

Figure 5:
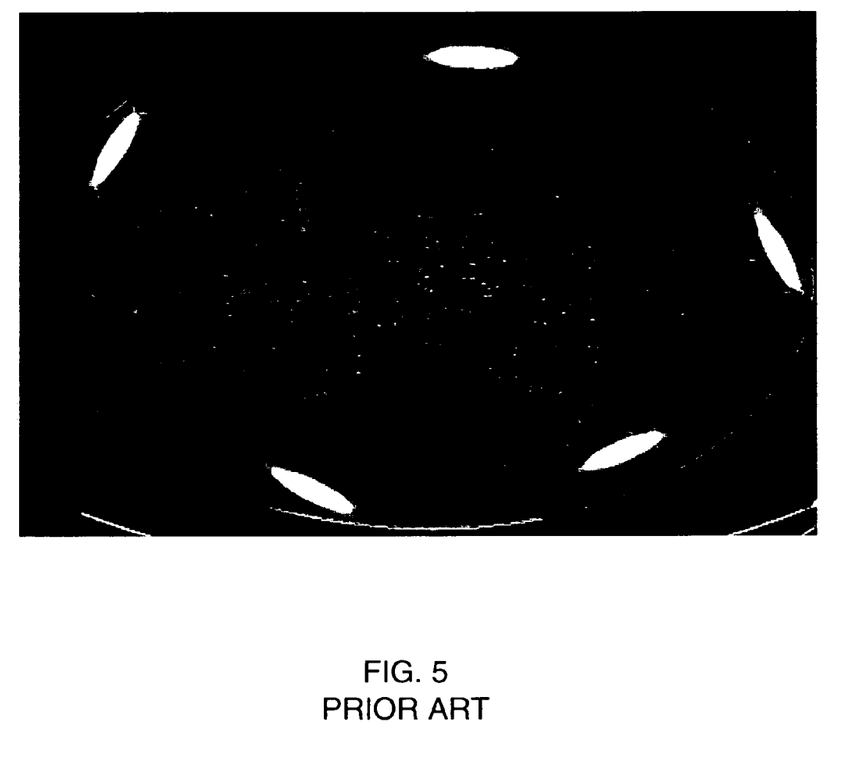
FIG. 5 is a reconstructed image of a 16×1.25 mm acquisition utilizing a prior art Feldkamp algorithm, wherein the slice is 8.125 mm above a center plane, with ww=400.

For example, for a CT system with S=541 mm, R=250 mm, and D=20 mm, the cylindrical volume that can be covered by each axial scan is only 10.8 mm. To obtain a continuous coverage of an organ, the distance between adjacent scans is limited to 10.8 mm, which is roughly half the detector z-coverage at the isocenter. To reconstruct a volume of 20 mm, extrapolation has to be performed to utilize the FDK (Feldkamp) reconstruction algorithm. However, this extrapolation introduces artifacts into the reconstructed image. For example, FIG. 5 shows an image reconstructed from a 16×1.25 mm axial mode scan. The depicted image is located 9.375 mm above a center plane of the fan beam. Shading artifacts are clearly observable near the simulated ribs.

Figure 6:
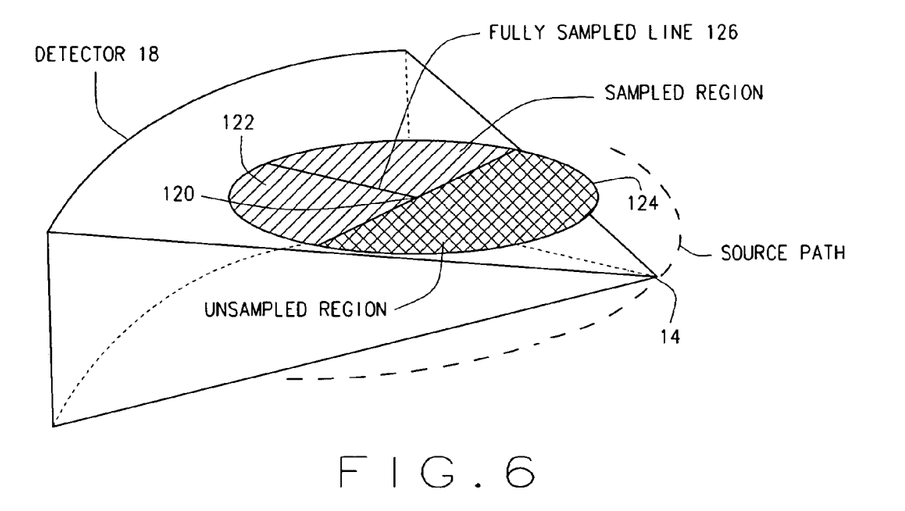
FIG. 6 is another illustration of the geometry of reduced volume coverage in step-and-shoot mode.

To avoid the introduction of artifacts in image reconstruction, some configurations of the present invention avoid projection extrapolation. For example and referring to FIG. 6, consider a case in which the original cone beam data is rebinned to a set of tilted parallel beam samples. For image slices near the top and bottom of the scanned volume, each projection illuminates only half 122 of circular region 124 the reduced volume coverage of a step-and-shoot multi-slice CT imaging system is shown. Referring to FIG. 6, the minimum angular range for a complete reconstruction is 180° for parallel geometry. Thus, the portion of data that is fully sampled by an entire 180° projection is a line 126 centered on the range of projection. Thus, the only region that can be fully supported by any 180° range of projection data is only line 126. The consequence for reconstruction is that for each radial line that radiates from isocenter 120, a different 180° projection data set is required. No two lines should be using exactly the same dataset.

Figure 7:
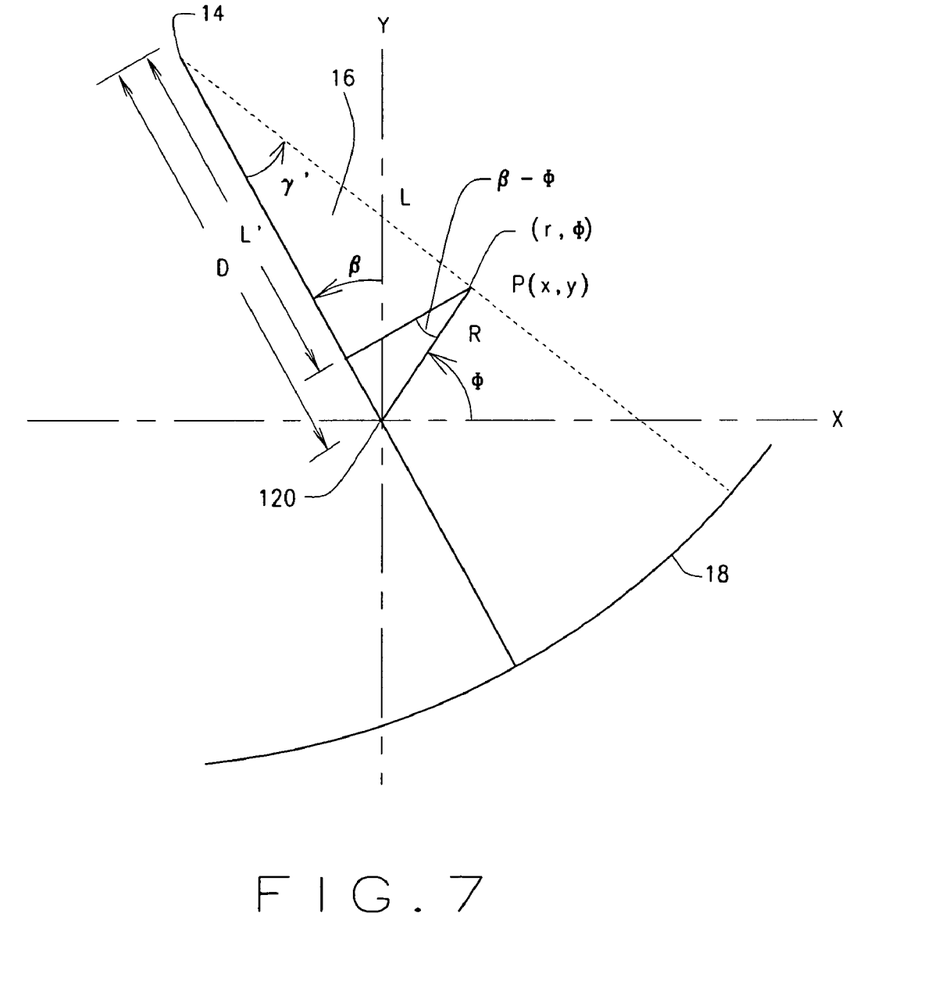
FIG. 7 is an illustration of the geometry of a configuration of a CT imaging system, wherein certain variables used herein are defined by illustration.

To perform a reconstruction in which a different 180° projection data set is used for each radial line radiating from isocenter 120, some configurations of the present invention perform reconstruction in a polar coordinate system rather than a Cartesian coordinate system. For each plane segment, only projection views at an angle less than 90° from a plane angle are used to contribute to pixels in the plane segment. Thus, no extrapolation is needed during backprojection. Referring to FIG. 7, reconstruction is performed in accordance with an expression written as:

$$f(r,\phi,z) = \int_{\phi-\pi/2}^{\phi+\pi/2} \int_{-\infty}^{+\infty} P(\omega,\theta,z')|\omega|e^{j2\pi\omega t}\,d\omega\,d\theta, \quad (1)$$

where $P(\omega,\theta,z')$ is the Fourier transform of the cone-beam rebinned and weighted projection at projection angle $\theta$, and $z'$ is the projected height of point $(r,\phi,z)$ in the tilted parallel beam geometry.

Figure 8:
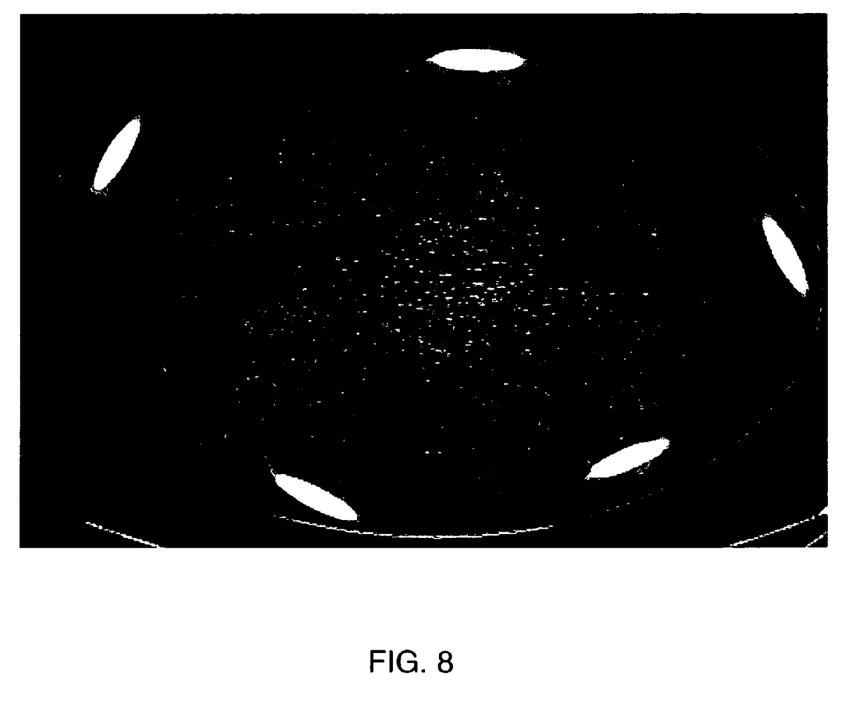
FIG. 8 is a reconstructed image with 180° only projection.
Figure 9:
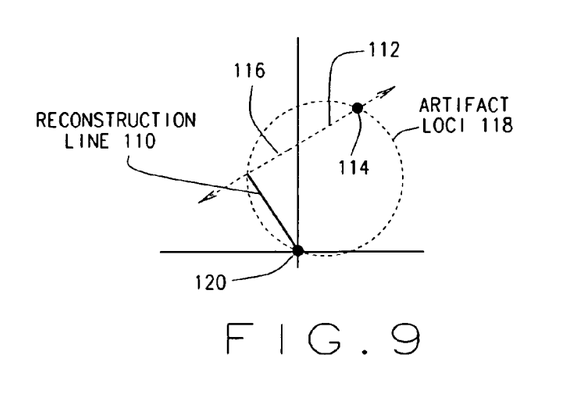
FIG. 9 is an illustration of the source of artifacts visible in FIG. 8.
Figure 10:
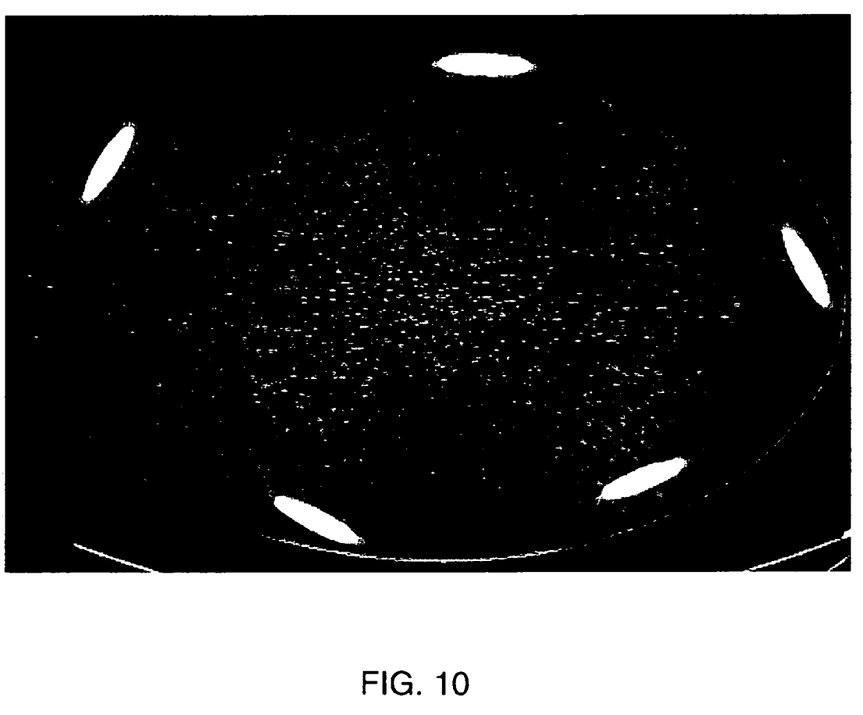
FIG. 10 is an illustration of a reconstructed image utilizing a configuration of the present invention, with ww=400.

Although this approach avoids extrapolation, image artifacts can be produced, as shown in FIG. 8. Unlike a parallel beam geometry, projection data of a tilted projection that are 180° apart are not identical. Thus, samples that are 180° apart are not redundant samples as is in a parallel beam case. This inconsistency or difference can result in artifacts in the reconstructed images. For a conventional reconstruction in which exactly 180° angles are used, the shading artifacts line up with the projection angle between the first and last projections 180° apart. The artifact appears as a line. However, in configurations of the present invention, the projection angular range used in an image is location-dependent. For example, and referring to FIG. 9, for a reconstruction line 110, two end projections used for a reconstruction are lined up with arrow 112. The greatest amount of inconsistency occurs on a high-density object with variation in z, such as a rib in a patient (or in a phantom) represented by circle 114. Therefore, the artifact produced on reconstructed line 110 is the intersection of reconstructed line 110 with dotted line 116 passing through circle 114. Artifacts produced in all reconstruction lines form a circle 118 that passes through both isocenter 120 and circle 114.

Thus, in some configurations of the present invention, to produce an image of an object, a computed tomography (CT) imaging system having a radiation source and a detector array is used to axially scan an object to obtain more than 180° of projection data. The projection data is weighted according to projection location in various configurations and pixel location in an image to be reconstructed, for example as indicated by eq. (1). An image of the object is reconstructed utilizing the weighted projection data.

The largest inconsistency is produced by projections that are 180° apart. Thus, in some configurations of the present invention, the contributions of projections 180° apart are reduced in the formation of an image. Instead, more than 180° of projection data are used and the projections are weighted in accordance with their location and reconstructed image pixel location. Thus, in some configurations of the present invention, reconstruction is performed in accordance with a relationship written as:

$$f(r, \phi, z) = \int_{\phi-\Gamma}^{\phi+\Gamma} \int_{-\infty}^{\infty} w(\phi-\theta) P(\omega, \theta, z') |\omega| e^{j2\pi\omega t} d\omega d\theta \quad (2)$$

wherein the weight $w(\phi-\theta)=w(\alpha)$ is defined by a relationship written as:

$$w(\alpha) = \begin{cases} 1 - 3\left|\frac{\alpha}{\eta}\right|^2 - 2\left|\frac{\alpha}{\eta}\right|^3, & \text{if } |\alpha| \leq \eta \\ 1, & \text{otherwise,} \end{cases} \quad (3)$$

$\Gamma$ is a parameter that specifies the projection data range used in the reconstruction, and $\eta$ is a parameter that specifies a transition region.

In general, $\Gamma > \pi/2$. In some configurations, $\eta = \pi/4$. Resulting images using these values of parameters produce images having significantly reduced artifacts.

In some configurations of the present invention, polar coordinates are used for image reconstruction. If polar coordinates are used, the reconstructed images are interpolated into a Cartesian coordinate system for display. However, in other configurations, a Cartesian coordinate system is used with a location-dependent weighting function to limit the contribution of each projection to the reconstructed image to achieve the same effect. More particularly, the weighting of each cone-parallel rebinned projection to the reconstructed image is pixel-location dependent. Weighting of a projection for a part of an image closest to an x-ray source of the CT imaging system is less than the weighting of the other half of the image. For half of the image that is closer to x-ray source 14, little contribution is made. The net effect is the same as reconstructing the image with a polar coordinate system, but some configurations using Cartesian coordinate systems advantageously eliminate the second interpolation step to re-sample the reconstructed image back to Cartesian coordinates.

Thus, some configurations of the present invention utilize a CT imaging system to axially scan an object to obtain more than 180° of projection data of the object. The projection data are weighted according to projection location, and an image of the object is reconstructed utilizing the weighted projection data in a Cartesian coordinate system.

In still other configurations of the present invention, the weighting of projection data is limited to slices that are distant from a center plane. For slices close to the center plane of the fan beam, all of the projection data (360°) can be used without encountering the extrapolation issue. Thus, some configurations limit the projection data range to 180° only for image slices close to either end of the reconstruction volume. For slices between the center plane and the ends of the reconstruction volume, projection data is limited in some configurations to amounts greater than 180° but less than 360°. In configurations offering high signal to noise ratios, as much data as possible is used. Such configurations vary the parameter $\Gamma$ in equation (2) as a function of slice location.

Thus, some configurations utilize a computed tomography (CT) imaging system to axially scan an object to obtain more than 180° of projection data of the object. A range of projections is selected in accordance with locations of pixels of an image of the object to be reconstructed, and an image of the object is reconstructed utilizing the selected range of projections. In some configurations, selecting a range of projections comprises selecting a range of projections between $\phi-\pi/2$ to $\phi+\pi/2$, wherein $\phi$ is a polar angle of the pixels.

It will thus be appreciated that configurations of the present invention significantly reduce or eliminate objectionable cone beam artifacts in images produced from data obtained in axial CT scans. Thus, continuous coverage can be obtained with increased distance between adjacent axial scans relative to known methods and apparatus that attempt to reduce cone beam artifacts for moderate cone angles.

While the invention has been described in terms of various specific embodiments, those skilled in the art will recognize that the invention can be practiced with modification within the spirit and scope of the claims.

What is claimed is:

1. A method for producing an image of an object utilizing a computed tomography (CT) imaging system, said method comprising:

axially scanning an object utilizing the CT imaging system to obtain more than 180° of projection data of the object;

weighting the projection data according to projection location and pixel location in an image to be reconstructed; and reconstructing the image of the object utilizing the weighted projection data;

wherein said weighting the projection data according to the projection location comprises reducing the weighting of contributions of projections 180° apart to reconstructed image pixels and further wherein weighting the projection data comprises applying a weight $w(\phi-\theta)=w(\alpha)$ defined by a relationship written as:

$$w(\alpha) = \begin{cases} 1 - 3\left|\frac{\alpha}{\eta}\right|^2 - 2\left|\frac{\alpha}{\eta}\right|^3, & \text{if } |\alpha| \leq \eta \\ 1, & \text{otherwise,} \end{cases}$$

wherein $\eta$ is a parameter that specifies a transition region;

$\phi$ is an angle of an image pixel in a polar coordinate system; and $\theta$ is the projection angle.

2. A method in accordance with claim 1 wherein $\eta=\pi/4$.

3. A method in accordance with claim 1 wherein said reconstructing an image of the object utilizing the weighted projection data comprises reconstructing the image in accordance with a relationship written as:

$$f(r, \phi, z) = \int_{\phi-\Gamma}^{\phi+\Gamma} \int_{-\infty}^{\infty} w(\phi-\theta) P(\omega, \theta, z') |\omega| e^{j2\pi\omega t} d\omega d\theta$$

wherein Γ is a parameter that specifies the projection data range used in the reconstruction, and Γ>π/2.

4. A method in accordance with claim 3 wherein Γ is a function of image slice location relative to a center plane of a fan beam of a radiation source of the CT imaging system.

5. A method in accordance with claim 4 wherein Γ is larger for image slices closer to the center plane.

6. A method in accordance with claim 3 wherein η=π/4.

7. A method for producing an image of an object utilizing a computed tomography (CT) imaging system, said method comprising:
    axially scanning an object utilizing the CT imaging system to obtain more than 180° of projection data of the object;
    weighting the projection data according to projection location; and
    reconstructing an image of the object utilizing the weighted projection data;
    wherein weighting of a projection for a part of an image closest to a radiation source of the CT imaging system is less than the weighting of the other half of the image.

8. A method in accordance with claim 7 wherein said reconstructing an image of the object comprises reconstructing an image of the object utilizing the weighted projection data in a Cartesian coordinate system.

9. A method in accordance with claim 7 wherein said weighting the projection data comprises weighting the projection data according to projection location and pixel location.

10. A method for producing an image of an object utilizing a computed tomography (CT) imaging system, said method comprising:
    axially scanning an object utilizing the CT imaging system to obtain more than 180° of projection data of the object;
    selecting a range of projections in accordance with locations of pixels of an image of the object to be reconstructed; and
    reconstructing the image of the object utilizing the selected range of projections.

11. A method in accordance with claim 10 wherein selecting a range of projections comprises selecting a range of projections between $\phi-\pi/2$ to $\phi+\pi/2$, wherein $\phi$ is a polar angle of said pixels.

12. A computed tomography imaging system having a detector array and an radiation source, wherein to produce an image of an object, said system is configured to:
    axially scan an object to obtain more than 180° of projection data of the object;
    weight the projection data according to projection location and pixel location in an image to be reconstructed; and
    reconstruct the image of the object utilizing the weighted projection data;
    wherein to weight the projection data according to the projection location, said system is configured to reduce the weight of contributions of projections 180° apart to reconstructed image pixels; and wherein to weight the projection data, said system is configured to apply a weight $w(\phi-\theta)=w(\alpha)$ defined by a relationship written as:

$$w(\alpha) = \begin{cases} 1 - 3\left|\frac{\alpha}{\eta}\right|^2 - 2\left|\frac{\alpha}{\eta}\right|^3, & \text{if } |\alpha| \le \eta \\ 1, & \text{otherwise,} \end{cases}$$

wherein
    η is a parameter that specifies a transition region;
    φ is the angle of an image pixel in a polar coordinate system; and
    θ is the projection angle.

13. A system in accordance with claim 12 wherein η=π/4.

14. A system in accordance with claim 12 wherein to reconstruct an image of the object utilizing the weighted projection data, said system is configured to reconstruct the image in accordance with a relationship written as:

$$f(r, \phi, z) = \int_{\phi-\Gamma}^{\phi-\Gamma} \int_{-\infty}^{\infty} w(\phi - \theta) P(\omega, \theta, z') |\omega| e^{j2\pi\omega t} d\omega d\theta$$

wherein Γ is a parameter that specifies the projection data range used in the reconstruction, and Γ>π/2.

15. A system in accordance with claim 14 wherein Γ is a function of image slice location relative to a center plane of a fan beam of the radiation source of the CT imaging system.

16. A system in accordance with claim 15 wherein Γ is larger for image slices closer to the center plane.

17. A system in accordance with claim 14 wherein η=π/4.

18. A computed tomography imaging system having a detector array and an radiation source, wherein to produce an image of an object, said system is configured to:
    axially scan an object to obtain more than 180° of projection data of the object;
    weight the projection data according to projection location; and
    reconstruct the image of the object utilizing the weighted projection data;
    wherein weighting of a projection for a part of an image closest to a radiation source of the CT imaging system is less than the weighting of the other half of the image.

19. A system in accordance with claim 18 configured to reconstruct the image of the object utilizing the weighted projection data in a Cartesian coordinate system.

20. A system in accordance with claim 18 wherein said projection data is weighted according to projection location and pixel location.

21. A computed tomography imaging system having a detector array and an radiation source, wherein to produce an image of an object, said system is configured to:
    axially scan an object to obtain more than 180° of projection data of the object;
    select a range of projections in accordance with locations of pixels of an image of the object to be reconstructed; and
    reconstruct the image of the object utilizing the selected range of projections.

22. A system in accordance with claim 21 further configured to select said range of projections between $\theta-\pi/2$ to $\theta+\pi/2$, wherein $\theta$ is a polar angle of said pixels.

* * * * *